United States Patent [19]
Corsi

[11] Patent Number: 5,811,457
[45] Date of Patent: Sep. 22, 1998

[54] THERAPEUTICAL METHOD FOR TREATING CHRONIC ARTERIOSCLEROSIS OBLITERANS

[75] Inventor: Marco Corsi, Rome, Italy

[73] Assignee: Sigma-Tau Industrie Farmaceutiche Riunite S.p.A., Rome, Italy

[21] Appl. No.: 714,424

[22] Filed: Sep. 16, 1996

[30] Foreign Application Priority Data

Mar. 4, 1996 [EP] European Pat. Off. .............. 96830093

[51] Int. Cl.⁶ ................................................. A61K 31/225
[52] U.S. Cl. ............................................................ 514/547
[58] Field of Search ............................................. 514/547

[56] References Cited

U.S. PATENT DOCUMENTS 4,343,816   8/1982   Cavazza ................................... 514/556
4,968,719   11/1990  Brevetti ................................... 514/556

OTHER PUBLICATIONS

Dialog On–line Print of Sigma–Tau Research and Development (R&D) update, 1991.

*Primary Examiner*—Raymond Henley, III
*Attorney, Agent, or Firm*—Oblon, Spivak, McClelland, Maier & Neustadt, P.C.

[57] ABSTRACT

A therapeutical method for treating chronic arteriosclerosis obliterans in particularly selected patients with severely disabling intermittent claudication is disclosed, which comprises administering propionyl L-carnitine or a pharmacologically acceptable salts thereof.

10 Claims, 2 Drawing Sheets

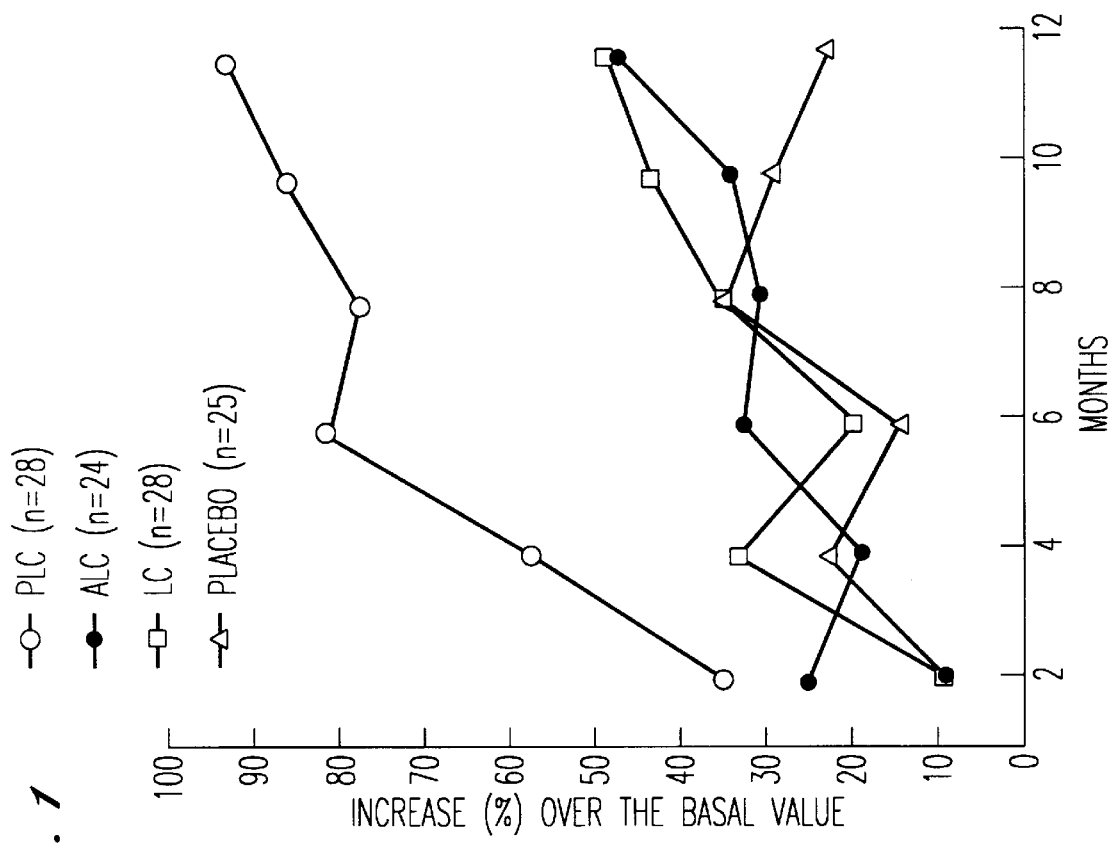
FIG. 1
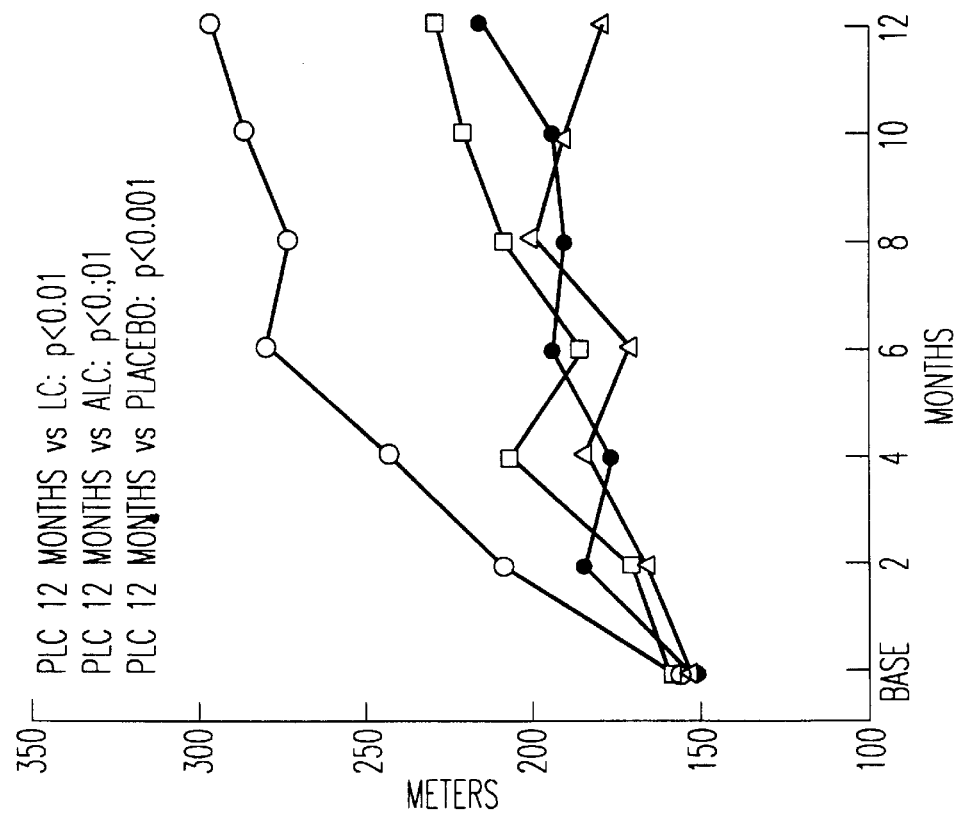

THERAPEUTICAL METHOD FOR TREATING CHRONIC ARTERIOSCLEROSIS OBLITERANS

BACKGROUND OF THE INVENTION

1. Field of the Invention

The present invention relates to a therapeutical method for treating patients suffering from chronic arteriosclerosis obliterans at stage II of Leriche Fontaine's classification.

More specifically, the present invention relates to a therapeutical method for the selective treatment of those patients showing the symptom of a severely disabling intermittent claudication (hereinbelow shortly referred to as "patients with intermittent claudication") wherein the expression "severely disabling" shall be subsequently rigorously defined with reference to the guidelines on the efficacy of candidate drugs issued by the Regulatory Authorities on medicinal products.

2. Description of the Prior Art

As known and widely accepted, the various stages of chronic arteriosclerosis obliterans are rated following Leriche Fontaine's classification which is based on the assessment of clinical parameters. This classification places at the II stage thereof the patients with intermittent claudication who do not experience pain at rest and with no trophic lesions in the affected limb.

Among the symptoms shown by patients suffering from arteriosclerosis obliterans, intermittent claudication, brought about by a deficient blood supply in the exercising muscles of lower limbs, is the main symptom in view of its severe impact on all the many-sided features of that complex entity concisely termed "quality of life".

Moreover, patients with intermittent claudication must be rated a high risk population for the development of clinical manifestations of cardiovascular disorders.

Intermittent claudication is described as a pain, ache, cramp and tired feeling; it occurs on walking most commonly in the calf, but also in the foot, thigh, hip or buttocks. The onset of intermittent claudication is shortened by walking rapidly or uphill, whereas the symptom can be alleviated and even disappear following some minutes of rest.

Progression of the obliterans disease is indicated by the steadily diminishing distance the patient can walk before pain onset and the distance the patient can walk before unbearable pain forces him (or her) to rest. Consequently, as guiding parameters for both patients inclusion in controlled clinical trials and assessment of data of clinical trials aimed at evaluating the efficacy of a candidate drug, the following have become more and more relevant: the initial claudication distance, ICD, or pain-free walking distance, PFWD, defined as the distance the patient is able to walk before pain onset, and the maximal walking distance (MWD), i.e. the distance in meters covered by the patient before being forced to rest.

To ensure optimum reproducibility among test results, both ICD and MWD are recorded while the patient walks, under standardized environment conditions, on a tread-mill moving backwards to the patient's walking direction at about 4 km/h. Tread-mill inclination may be varied and reach 7° with respect to the floor.

Despite the relevance of the social and economical impact of chronic arteriosclerosis obliterans (intermittent claudication affects 5% of the male population of more than 50 years of age), to date there are no drugs on the market which are suitable to achieve the therapeutical goal of increasing the patient's walking capacity by improving the balance between energy supply and metabolic demand in the ischaemic skeletal muscle.

The registered drug at present most widely marketed for the symptomatic treatment of intermittent claudication is pentoxifylline, a vasodilator whose actual efficacy has been seriously questioned (see e.g., Donaldson D R., Hall T J., Kester R C., Ramseden C W., Wiggins P A., Does pentoxifylline have a place in the treatment of intermittent claudication? Curr. Med. Res. Opin 1984; 9: 35–40). Consequently, the authoritative Drug Information, published by the American Society of Hospital Pharmacists concludes that: "Pentoxifylline has been reported to produce greater reductions in severity and occurrence of paresthesia and trophic ulcers than does placebo: however, the drug does not appear to be more effective than placebo in relieving other symptoms associated with claudication such as cramping, tiredness, tightness, and pain during exercise (Drug Information 88, pag. 753).

The increasing distrust of the Regulatory Authorities towards pentoxifylline is substantiated by the fact that these Authorities do not require that controlled clinical trials be conducted with pentoxifylline as reference drug, whereas the candidated drug is expected to show efficacy over placebo.

As regards patent literature, U.S. Pat. No. 4,343,816 discloses the use of acyl derivatives of DL-, D- or L-carnitine wherein the acyl group contains 2–20 carbon atoms (such as e.g. acetyl, propionyl, butyryl and acetoacetylcarnitine) for treating peripheral vasculopathies. This patent, wherein intermittent claudication is not even mentioned and wherein the therapeutical goal of improving parameters such as ICD and MWD is not tackled at all, emphasizes the use of acetylcarnitine for treating functional arterial diseases, such Reynaud's disease.

U.S. Pat. No. 4,968,719 discloses the use of L-carnitine and pharmacologically acceptable salts thereof for treating peripheral vasculopathies, among which intermittent claudication is mentioned. The clinical data reported therein point out an improvement in the walking performances of L-carnitine-treated patients. However, these data were obtained from an indifferentiated patient population as regards the varying degree of severity of intermittent claudication. In view of the fundamental reasons hereinbelow discussed, these data cannot be, therefore, related to those achieved in accordance with the present invention.

In fact, in order to thoroughly evaluate the innovative character and the therapeutical advantages afforded by a novel drug, the state of the relevant prior art should be supplemented with the guidelines adopted by The Regualtory Authorities that starting from a more developped knowledge of the disease dealt with lay down criteria more and more targeted and severe for conducting controlled clinical trials aimed at assessing the actual efficacy of a candidate drug.

As regards the guidelines relating to the drugs for treating chronic arteriosclerosis obliterans and specifically for treating patients with intermittent claudication, reference is made to the "Note for Guidelines on the Clinical Investigation of Medicinal Products in the Treatment of Chronic Peripheral Arterial Occlusive Disease" (CPMP/EWP/233/95) recently adopted by The European Agency for the Evaluation of Medicinal Products (Human Medicines Evaluation Unit).

These guidelines not only stress that the primary endpoint for chronic arteriosclerosis obliterans at stage II of Leriche Fontaine's classification are ICD and MWD and not others, but recommend that tests be conducted under the aforesaid standardized conditions, aimed at singling out those patients who are suitable for inclusion in the clinical trial, by complying with the following criteria:

(1) The maximum change between two MWD tests performed at fixed time intervals should be less than 25% during the run-in phase;
(2) MWD should be shorter than 300 meters, preferably between 100 and 300 meters.

The selective inclusion of patients with MWD shorter than 300 meters only (who, therefore, can be properly termed patients with severely disabling intermittent claudication) aims at avoiding that walking distances of more than 300 meters may alter the results of the trial because of the development of the "walking-through" phenomenon. This term refers to some patients'endurance and capacity to keep on walking in spite of an extremely severe pain. On the other hand also patients with MWD shorter than 100 meters should be excluded from the trial since they may influence the results due to their greater tendency towards progression.

Consequently, whenever an amelioration in patients so selectively singled out is observed, corroborating evidence of the therapeutical efficacy of the candidate drug has been achieved.

It is, therefore, an object of the present invention to provide a therapeutical method for the treatment of chronic arteriosclerosis obliterans at stage II of Leriche Fontaine's classification in patients with maximal walking distance (MWD) shorter than 300 meters.

More particularly, it is the object of the present invention to provide a therapeutical method for the treatment of chronic arteriosclerosis obliterans at stage II of Leriche Fontaine's classification characterized in that the method is selectively suited for treating patients with intermittent claudication fulfilling the inclusion criteria in controlled clinical trials set forth in the CPMP/EWP/233/95 guidelines.

SUMMARY OF THE INVENTION

It has now been found that within the class of compounds consisting of L-carnitine and the known, aforesaid acyl derivatives of L-carnitine, selectively propionyl L-carnitine and the pharmacologically acceptable salts thereof are particularly effective (furnishing statistically significant data) for treating patients suffering from chronic arteriosclerosis obliterans at stage II of Leriche Fontaine's classification who fulfill the stringent criteria for recruitment in controlled clinical trials set forth in the CPMP/EWP/233/95 guidelines issued by the European Agency for the Evaluation of Medicinal Products.

Therefore, the method of the present invention comprises orally, parenterally or intravenously administering to patients suffering from chronic arteriosclerosis obliterans at II of Leriche Fontaine's classification and with maximal walking distance (MWD) shorter than 300 meters an amount of propionyl L-carnitine or a pharmacologically acceptable salt thereof effective for ameliorating their MWD.

BRIEF DESCRIPTION OF THE DRAWINGS

FIG. 1 consists of two graphs showing maximal walking distance (MWD) in 105 patients with severely disabling intermittent claudication as a function of time in months.

DESCRIPTION OF SPECIFIC EMBODIMENTS

It was, furthermore, found that although the daily dose to be administered is determined from the age, weight and condition of the patient, utilizing sound professional judgement, it is generally advisable to administer 1–4 g/day, preferably 2–3 g/day, of propionyl L-carnitine or an equivalent molar amount of a pharmacologically acceptable salt thereof. Larger doses can be safely administered in view of the extremely low toxicity of propionyl L-carnitine.

A clinical study showing the efficacy of propionyl L-carnitine is hereinbelow described.

Patients at least 40 years of age were recruited for this study. All patients had a history of intermittent claudication of at least one year in duration.

The diagnosis of chronic arteriosclerosis obliterans was established by clinical examination, Doppler examination and decrease in ankle/arm systolic blood pressure ratio (ankle/brachial index or Windsor's index) after exercise. To ensure that patients admitted to the study had a sufficiently stable walking capacity, three treadmill tests were conducted on each patient during the run-in phase at 15-day intervals (following a 2-week wash-out period during which the administration of any drug for treating arteriosclerosis obliterans was suspended).

The treadmill was set at a speed of 4 km/hour and an inclination of 7°.

Only patients whose MWD between the three tests varied less than 25%, had MWD from 100 to 250 meters and Windsor's index lower than 0.8 were enrolled in the study. 105 patients were thus included in the study, who were randomized in the following four groups:

Group a. 28 patients treated with propionyl L-carnitine (2 g/day oral, for 12 months);
Group b. 24 patients treated with acetyl L-carnitine (2 g/day oral, for 12 months);
Group c. 28 patients treated with L-carnitine (2 g/day oral, for 12 months);
Group d. 25 patients treated with placebo (oral, for 12 months).

The characteristics of the patients of the four groups were the following:
Group a. (20 male/8 female) 61±6 years of age, 4 diabetics, history of intermittent claudication of 14±5 months.
Group b. (22 male/2 female) 61±8 years of age, 3 diabetics, history of intermittent claudication of 18±8 months.
Group c. (19 male/9 female) 58±9 years of age, 5 diabetics, history of intermittent claudication of 15±4 months.
Group d. (20 male/5 female) 63±6 years of age, 4 diabetics, history of intermittent claudication of 16±5 months.

Both ICD and MWD of each patient were measured after 2, 4, 6, 8, 10 and 12 months after start of treatment using the same procedures and under the same conditions as those of the basal values. At the same time intervals the ankle/brachial index (Windsor's index) was evaluated.

Samples of blood were drawn and urines were collected to monitor safety and tolerability of the administered drugs.

Figure 2:
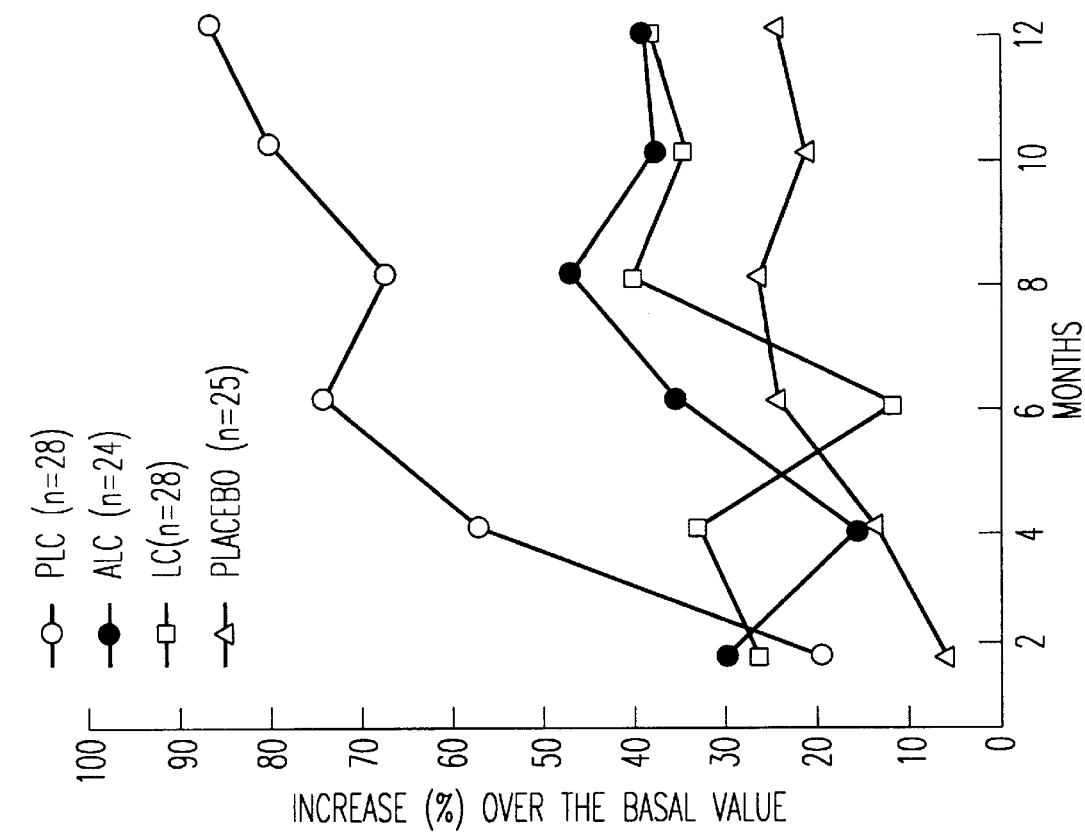
FIG. 2 is similar to FIG. 1 except that initial claudication distance (ICD) is shown instead of MWD.
Figure 2:
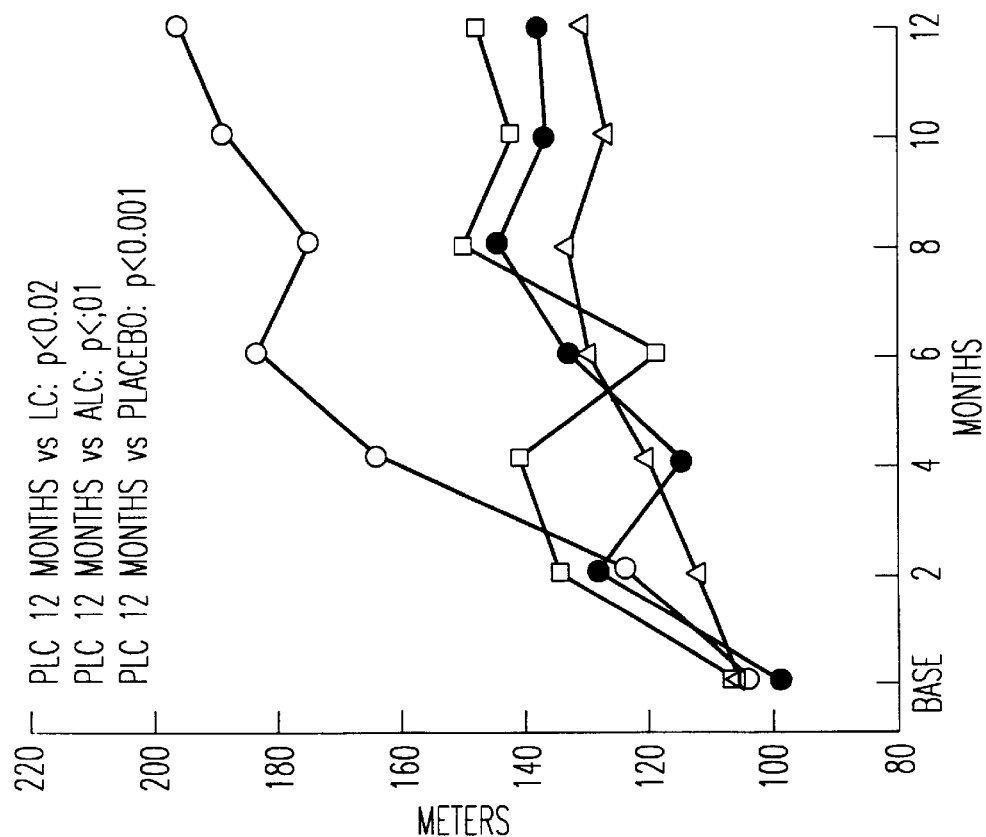

The results of the clinical study are illustrated in the graphs of FIG. 1 and 2.

At the end of the 12-month treatment (see FIG. 1), MWD of group "a" (propionyl L-carnitine, PLC) was 305±120 meters. This value was statistically higher than that of group "b" (acetyl L-carnitine, ALC, 223±1147 meters, p<0.01), group "c" (L-carnitine, LC, 237±156 meters, p<0.02) and group "d" (placebo, 188±173, p<0.001).

MWD of both group "b" (ALC) and group "c" (LC) was not statistically higher than that of group 'd" (placebo).

At the end of the twelfth month, MWD of group "a" (PLC) was 95%, group "b" (ALC) 44%, group "c" (LC) 43% and group "d" (placebo) 28% higher than basal value.

It was utterly apparent that the clinical response of group "a" (PLC) was fully significant between the 4th and the 6th month of treatment already (see FIG. 1, $p<0.05$ and $p<0.02$, respectively).

ICD progress paralleled that observed for MWD (see FIG. 2).

During the study, no remarkable modifications of the Windsor's index, safety and tolerability parameters were observed in any of the four groups.

The medicament of the present invention can be prepared by mixing the active ingredient (propionyl L-carnitine or a pharmacologically acceptable salt thereof with excipients suitable for the formulation of compositions which lend themselves to enteral administration (particularly oral administration) or to parenteral administration (particularly by the intramuscular or intravenous route). All such excipients shall be readily apparent to one having ordinary skill in this art.

Pharmaceutically acceptable salts of propionyl L-carnitine include all pharmaceutically acceptable salts which are prepared by the addition of an acid to L-carnitine, and which do not give rise to undesired toxic or side effects. The formation of pharmaceutically acceptable acid addition salts is well known in pharmaceutical technology.

Non-limiting examples of suitable salts include the chloride, bromide, orotate, acid aspartate, acid citrate, acid phosphate, fumarate, acid fumarate, lactate, maleate, acid maleate, acid oxalate, acid sulphate, glucose phosphate, tartrate and acid tartrate salts. Other suitably acceptable salts which are nontoxic and provide substantially similar results to administration of propionyl L-carnitine and the above-identified pharmaceutical salts will be readily apparent to one having ordinary skill in the art and are considered to be equivalent to the salts enumerated above.

Some example of compositions in unit dosage form are hereinbelow described.

(a) Composition for tablets
one tablet contains:
Active ingredient
  propionyl L-carnitine HCl mg 500
Excipients
  microcrystalline cellulose mg 54,0
  polyvinylpyrrolidone mg 18,0
  crospovidone mg 30,0
  magnesium stearate mg 15,0
  precipitated silica mg 3,0
  hydroxypropylmethylcellulose mg 10,0
  polyethyleneglycol 6000 mg 2,5
  titanium dioxide mg 1,8
  methacrylate copolymer mg 8,3
  purified talc mg 2.4

(b) Composition for intravenously injectable vials
one vial contains:
Active ingredient
  propionyl L-carnitine HCl mg 300
Excipients
  mannitol mg 300
One vial of solvent contains:
  sodium acetate.$3H_2O$ mg 390
  water for injection q.s. to ml 5.

What is claimed is:

1. A therapeutical method for the treatment of chronic arteriosclerosis obliterans at stage II of Leriche Fontaine's classification in patients with maximal walking distance (MWD) equal to or greater than 100 meters and shorter than 300 meters which comprises orally, parenterally or intravenously administering to the patients an amount of propionyl L-carnitine or a pharmacologically acceptable salt thereof effective for ameliorating their MWD.

2. A therapeutical method for ameliorating the maximal walking distance (MWD) in patients suffering chronic arteriosclerosis obliterans at stage II of Leriche Fontaine's classification with maximal walking distance (MWD) equal to or greater than 100 meters and shorter than 300 meters which comprises orally, parenterally or intravenously administering to the patients an amount of propionyl L-carnitine or a pharmacologically acceptable salt thereof.

3. The method of claim 1 or 2 which comprises orally, parenterally or intravenously administering 1–4 g/day of propionyl L-carnitine or an equivalent molar amount of a pharmacologically acceptable salt thereof.

4. The method of claim 1, wherein the pharmacologically acceptable salt of propionyl L-carnitine is selected from chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

5. The method of claim 2, wherein the pharmacologically acceptable salt of propionyl L-carnitine is selected from chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

6. The method of claim 3, wherein the pharmacologically acceptable salt of propionyl L-carnitine is selected from chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

7. The method of claim 1 which comprises orally, parenterally or intravenously administering 2–3 g/day of propionyl L-carnitine or an equivalent molar amount of a pharmacologically acceptable salt thereof.

8. The method of claim 2 which comprises orally, parenterally or intravenously administering 2–3 g/day of propionyl L-carnitine or an equivalent molar amount of a pharmacologically acceptable salt thereof.

9. The method of claim 7, wherein the pharmacologically acceptable salt of propionyl L-carnitine is selected from chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

10. The method of claim 8, wherein the pharmacologically acceptable salt of propionyl L-carnitine is selected from chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

* * * * *